Dec. 8, 1959 H. C. SWIM Plant Pat. 1,883
PEACH TREE
Filed Nov. 25, 1958
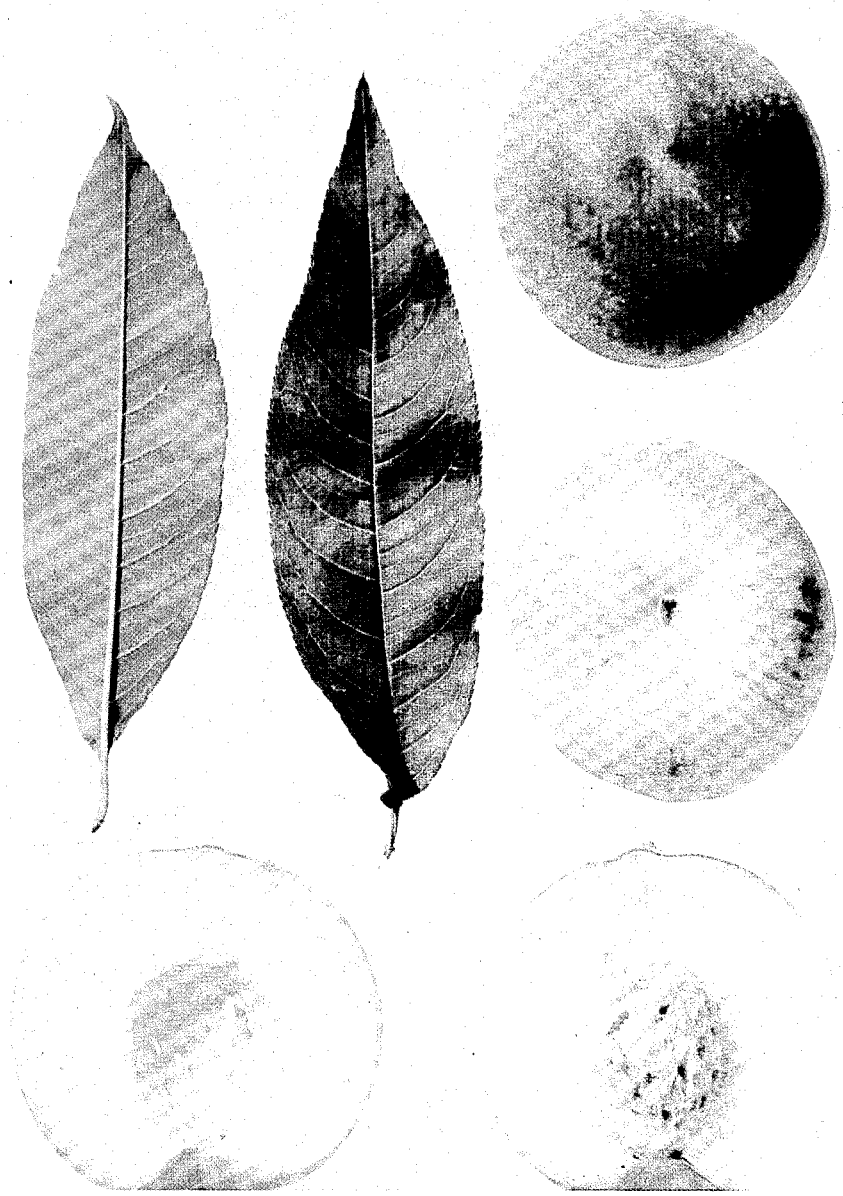
Inventor.
H. C. Swim
By: Cobb & Cobb
Attorneys.

United States Patent Office

Plant Pat. 1,883
Patented Dec. 8, 1959

1,883

PEACH TREE

Herbert C. Swim, Ontario, Calif., assignor to Armstrong Nurseries, Inc., Ontario, Calif., a corporation of California Application November 25, 1958, Serial No. 776,248

1 Claim. (Cl. 47—62)

The present invention relates to a new and distinct variety of peach tree of the yellow-fleshed, semi-freestone, fruit-bearing type, which was originated by me by crossing two unnamed and unpatented peach varieties. The unnamed seed parent was originally derived from a cross of "Luken's Honey" (unpatented) × "July Elberta" (Plant Patent No. 15), while the pollen parent was derived from a cross of the same ancestors as produced the seed parent, with a further cross thereof with "Robin" (Plant Patent No. 529).

The primary objective of this breeding was to produce a very early peach variety of the yellow-fleshed fruit type. This objective was fully achieved, along with other desirable improvements, including attractive appearance and high quality of the fruit, as attained by combining the earliness factors inherent in both parents, although exhibited only in the pollen parent, with the yellow-fleshed fruit factors inherent in both parents, but exhibited only in the seed parent. As the result, the new variety is particularly characterized as to novelty by the following unique combination of outstanding features which distinguish the new variety from its parents, as well as from all other varieties of which I am aware:

(1) A vigorous habit of growth, combined with a chilling requirement about equal to or slightly less than that of "Springtime" peach (Plant Patent No. 1,268) which is a white-fleshed peach;

(2) Medium-sized, yellow-fleshed, semi-freestone fruit, combined with a "peach" flavor having a balanced blend of acidity and sweetness; and (3) A fruit-ripening habit which is generally about 3 days to one week later than that of "Springtime" peach in southern California and falls from about the middle to late May or early June, thus making it the earliest ripening yellow-fleshed peach ever available.

In addition to the fact that the fruit of the new variety is yellow-fleshed and generally ripens slightly later than the white-fleshed fruit of "Springtime," the new variety has a maturation period averaging from about 5 to 7 days shorter than that of "Robin" (also a white-fleshed peach), and a considerably lower chilling requirement than that of "Robin," which results in ripening of the fruit of my new variety from about 2 to 3 weeks earlier than "Robin" in southern California. The fruit of the new variety averages somewhat smaller in size than that of "Blazing Gold" (Plant Patent No. 1,127), but has a shorter maturation period of about 5 to 10 days, and a lower chilling requirement, resulting in ripening of the fruit of the new variety from 2 to 3 weeks earlier than that of "Blazing Gold" in southern California.

Asexual reproduction of the new variety by grafting, as performed at Ontario, California, shows that the foregoing characteristics and distinctions come true to form and are established and transmitted through succeeding propagations.

The accompanying drawing shows typical specimens of the foliage and fruit of my new variety, with the upper and lower surfaces of the foliage being illustrated, and with both exterior and sectional views of the fruit being shown, all as depicted in color as nearly true as it is reasonably possible to make the same in a color illustration of this character.

The following is a detailed description of my new variety, as based upon observations of specimens grown at Ontario, California, with color terminology in accordance with Robert F. Wilson's Horticultural Colour Chart (hereinafter abbreviated as "Wilson") and Ridgway's Color Standards and Nomenclature (hereinafter abbreviated as "Ridgway"), except where general color terms of ordinary dictionary significance are obvious:

*Tree*

Habit: Vigorous; upright-spreading.
Fruit production: Good; regular bearer.
Current growth:
- *Surface texture.*—Smooth at first, with lenticels small and minute. With age larger, cracked, slightly raised lenticels appear toward base of more vigorous shoots.
- *Color.*—Green or slightly reddish at first on exposed surfaces, with lenticels appearing as small, nearly white dots; becomes brown with age.

2-year wood:
- *Surface texture.*—Generally smooth, with slightly raised, irregular, longitudinal striations and numerous lenticels.
- *Color.*—From greenish brown to brown.

Old wood:
- *Surface texture.*—Generally smooth, with moderate number of large, raised lenticels and occasional deep longitudinal fissures.
- *Color.*—From grey to greyish brown or reddish brown on more exposed surfaces.

Leaves:
- *Size.*—Length—from 5 inches to 6½ inches. Width—from 1½ to 1¾ inches.
- *Shape.*—Lanceolate, with apex acuminate.
- *Color.*—Upper surface—dark green. Lower surface—lighter green.
- *Petiole.*—Medium length.
- *Margin.*—From finely serrate to somewhat crenate; glandular.
- *Glands.*—Mixed type, although generally more reniform; medium size; usually from 3 to 5 in number; borne both on the petiole and on the base of the blade; arranged both opposite and alternate.

Vegetative buds:
- *Size.*—Small.
- *Shape.*—Ovoid, unless compressed between flower buds.
- *Color.*—Dark brown, with thick pubescence of moderate length.

*Flowers*

Dates of first and full bloom: Over prolonged period of observation, varied widely from about February 5th to March 5th for first bloom, and from about February 13th to about March 15th for full bloom, due to weather variations from year-to-year.

Dormant flower buds:
- *Shape.*—Ovoid.
- *Scales.*—Pubescent.
- *Color.*—Dark brown.

Size (when fully open): Non-showy; medium.
Petalage: Single; usually 5 petals.
Color (open flower): Between Neyron Rose, Plate 623/1, page 76 (Wilson) and Phlox Pink, Plate 625/1, page 77 (Wilson).

*Fruit*

Ripening dates: Generally ripens from about 3 days to one week after "Springtime" peach at Ontario, California, and usually from the middle to late May or early June; over a prolonged period of observations, the dates of first ripening ranged from May 13th to June 8th.

Maturity when described: Eating ripe.

Size: Somewhat variable, but generally medium sized.

*Axial diameter.*—From 2¼ inches to 2½ inches.

*Transverse diameter in suture plane.*—From 2¼ inches to 2½ inches.

*Transverse diameter at right angles to suture plane.*—From 2⅜ inches to 2⅝ inches.

Form: Somewhat variable, but broadly ovoid.

Suture: Usually a shallow, inconspicuous line extending from base to apex, with slight depression beyond pistil point.

Ventral surface: Generally rounded, and sometimes slightly lipped toward apex on one side.

Stem cavity: Rounded, but elongated slightly in suture plane, with suture showing on one side.

*Depth.*—About ¼ inch.

*Width.*—About ½ inch.

Base: Rounded.

Apex: Generally short and sometimes rounded, though prolonged in some seasons; pistil point from short to absent and apical.

Stem: Medium caliper; glabrous; medium adherence to stone. Length—from ¼ inch to ½ inch.

Skin:

*Thickness.*—From medium to thin.

*Texture.*—Medium.

*Tenacity to flesh.*—Frees easily.

*Pubescence.*—Moderate; medium length.

*Color.*—Base color varies between Buttercup Yellow, Plate 5/2, page 5 (Wilson) or Lemon Yellow, Plate 4/2, page 4 (Wilson) and Citron Green, Plate 763/3, page 100 (Wilson), streaked, flecked and blushed with between Delft Rose, Plate 020/1, page 108 (Wilson) and Delft Rose, Plate 020, page 108 (Wilson) and with near Claret Rose, Plate 021, page 109 (Wilson).

Flesh:

*Quality.*—Medium firm; melting; relatively fine, tender fibres.

*Aroma.*—Moderate.

*Flavor.*—Good, moderate, "peach" flavor, having a good balance between acidity and sweetness.

*Color.*—Near Lemon Yellow, Plate 4/2, page 4 (Wilson), except surface of pit cavity which is between Lemon Yellow, Plate 4/2, page 4 (Wilson) and Buttercup Yellow, Plate 5/2, page 5 (Wilson), with occasional flecks or slight streaks of Carmine, Plate 21/1, page 21 (Wilson) in the flesh or on the surface of the pit cavity.

Stone:

*Tenacity of flesh.*—Semi-free; generally adheres to flesh at least along ventral edge, and often retains short, fiberlike threads.

*Size.*—Length—about 1 inch. Width—about ¾ inch. Thickness—about ½ inch.

*Form.*—From ovoid to oblong.

*Base.*—Somewhat oblique.

*Hilum.*—Narrowly oval.

*Apex.*—Acuminate.

*Sides.*—Slightly unequal; irregularly furrowed and pitted throughout; ridges rounded; pits circular and sometimes elongated.

*Ventral edge.*—Medium thickness; with wing generally throughout.

*Dorsal edge.*—Medium thickness; with shallow groove; ridges on either side interrupted.

*Color.*—Near Cream Buff, Plate XXX (Ridgway), with some traces of Carmine, Plate 21/1, page 21 (Wilson) on surface of pits.

I claim:

A new and distinct variety of peach tree of the yellow-fleshed, semi-freestone, fruit-bearing type, substantially as herein shown and described, characterized particularly as to novelty by the unique combination of a vigorous habit of growth, a chilling requirement approximating that of the variety "Springtime" (Plant Patent No. 1,268), medium sized fruit having a good "peach" flavor and a balanced blend of acidity and sweetness, and an unusually early fruit-ripening habit falling from about the middle to late May or early June in the geographical area of southern California.

No references cited.